United States Patent [19]

Hamery et al.

[11] Patent Number: 6,068,079
[45] Date of Patent: *May 30, 2000

[54] ACOUSTIC VALVE CAPABLE OF SELECTIVE AND NON-LINEAR FILTERING OF SOUND

[75] Inventors: Pascal Hamery, Mulhouse; Armand Dancer, Sierentz; Georges Evrard, Durmenach, all of France

[73] Assignee: I.S.L. Institut Franco-Allemand de Recherches de Saint-Louis, Saint Louis, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/909,429

[22] Filed: Aug. 11, 1997

[30] Foreign Application Priority Data

Jul. 30, 1997 [FR] France ................. 97 09925

[51] Int. Cl.⁷ .......................................... A61B 7/02
[52] U.S. Cl. .......................... 181/135; 181/129; 181/130; 181/135; 381/372; 381/382; 128/864; 128/865; 128/866; 128/867; 128/868; 2/209

[58] Field of Search .................... 181/129, 130, 181/135; 381/372, 382; 128/864, 865, 866, 867, 868; 2/209

[56] References Cited

U.S. PATENT DOCUMENTS

| 2,465,606 | 3/1949 | Reynolds | 128/864 |
| 2,487,038 | 11/1949 | Baum | 181/135 |
| 2,619,960 | 12/1952 | Reynolds | 128/864 |
| 3,451,502 | 6/1969 | Branch et al. . | |
| 3,730,181 | 5/1973 | Fling | 128/864 |

FOREIGN PATENT DOCUMENTS

| 440572 | 8/1991 | European Pat. Off. . |
| 2050740 | 4/1971 | France . |

*Primary Examiner*—Khanh Dang
*Attorney, Agent, or Firm*—Cantor Colburn LLP

[57] ABSTRACT

Acoustic valve capable of selective and non-linear filtering of sound and placeable in a perforated ear plug. The acoustic valve consists of a tube enclosing two rigid disks axially spaced opposite each other, each of the disks containing at least one perforation. The total perforated surface of at least one disk is between 0.03 and 0.5 mm².

7 Claims, 1 Drawing Sheet

ACOUSTIC VALVE CAPABLE OF SELECTIVE AND NON-LINEAR FILTERING OF SOUND

BACKGROUND OF THE INVENTION

The object of this invention is an acoustic device capable of selective and non-linear filtering of sound, and placeable in the external auditory canal of a user by means of an earplug, and especially for use in a military or industrial environment.

One of the problems to be solved for those in the military is how to communicate between themselves, to detect, and localize and to identify the sources of exterior noises, all the while protecting their hearing against sudden noises, especially the high level noise of weapons (up to 190 dB SPL.)

There already exist ear plugs that one introduces into the auditory canal which greatly reduce, in the same manner, all sounds, whether they be sudden noise at a high level, environmental noise, or speech sounds at low levels.

The document FR-A-2050740 describes a noise filter, sensitive to a higher degree to the energy of language and to a lesser degree to background noise, and consisting of a capsule adapted to be inserted in a auditory canal of a user, and a vibrating element capable of discriminating frequencies positioned in the interior of the capsule, the filter also containing a diaphragm coupled to the vibrating element in an effective manner.

However, this device has a complex design and an elevated cost. In addition, the attenuation curves obtained from this device are not ideal for use in the military environment because it reduces low level noises and high level noises in the same manner.

The object of the document EP-A-0440572 is a sound transmitting device capable of selective filtering, and designed to be placed in the external auditory canal. This device consists of a tip, produced by molding from an imprint taken from the wearer and completely filling the external auditory canal. An acoustic valve is inserted into the tip. The device contains at least one acoustic valve placed at the end of a tube, and a section considerably larger than that of the tube. This valve plays the role of a resonance cavity, according to HELMHOLTZ'S resonator principle, the filter therefore being a filter of the fourth order of which the attenuation slope is 30 decibels per octave.

However, this device is of relatively complex design and presents a problem of capillary resistance due to the propagation of acoustic waves during their passage from the valve in the tube of smaller diameter which extends into the residual cavity. The result is that this acoustic filter device reduces in appreciably the same manner and identical intensity low level noises (human voice, environmental noise) and high level noises (sudden noise such as weapon noise.)

SUMMARY OF THE INVENTION

The present invention has for an aim to remedy these inconveniences by proposing an acoustic valve with a more simple design permitting improved filtering performance compared with known devices, notably at the level of non-linear acoustic performance of the filter. Moreover, the acoustic valve is particularly adapted to protect the user's eardrum against sudden sounds of high intensity, all the while letting pass intelligible sound waves representative of human speech and environmental noises of low levels.

The acoustic valve of the invention was designed after numerous studies and experiments seeking to obtain an efficient, non-linear behavior, and it is characterized by a tube containing two rigid disks spaced axially opposite each other by a distance between 2 and 7 mm, each of these disks presents at least one perforation, the total perforated surface of one disk being between 0.03 and 0.5 mm$^2$.

According to an additional characteristic of the invention, the thickness of the disks in the perforated zone is advantageously between 0.05 and 0.5 mm in order to avoid the appearance of a capillary resistance phenomenon.

In the preferred embodiment of the invention, the acoustic valve is made up of two hollow cylindrical parts each closed at one of their ends by a disk containing a central orifice, and open at their other end, the peripheral edge of which contains a shouldering wall allowing the assembly of two parts by the complementary open ends, attached by a means of fixation.

In other embodiments of the invention, one of the disks or both can be positioned at a distance from the end of the tube.

The acoustic valve of the invention is preferably constructed by molding a rigid plastic material such as an epoxy resin.

BRIEF DESCRIPTION OF THE DRAWING

The advantages and the characteristics of the invention will appear more clearly from the description which follows and which correlates to the attached drawing, provided by way of a simple illustration of the invention, in relation to which it does not present any limiting characteristics.

In the attached drawing.

DESCRIPTION OF THE PREFERRED EMBODIMENTS

Figure 1:
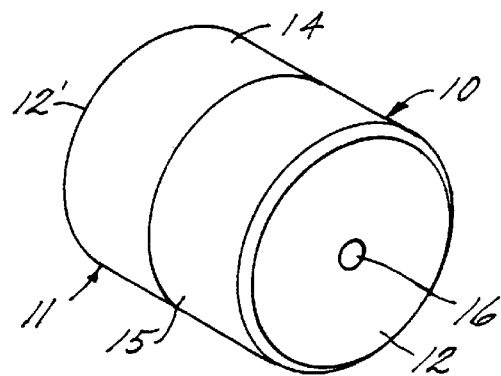
FIG. 1 represents a perspective view of a first embodiment of the acoustic valve according to the invention.
Figure 2:
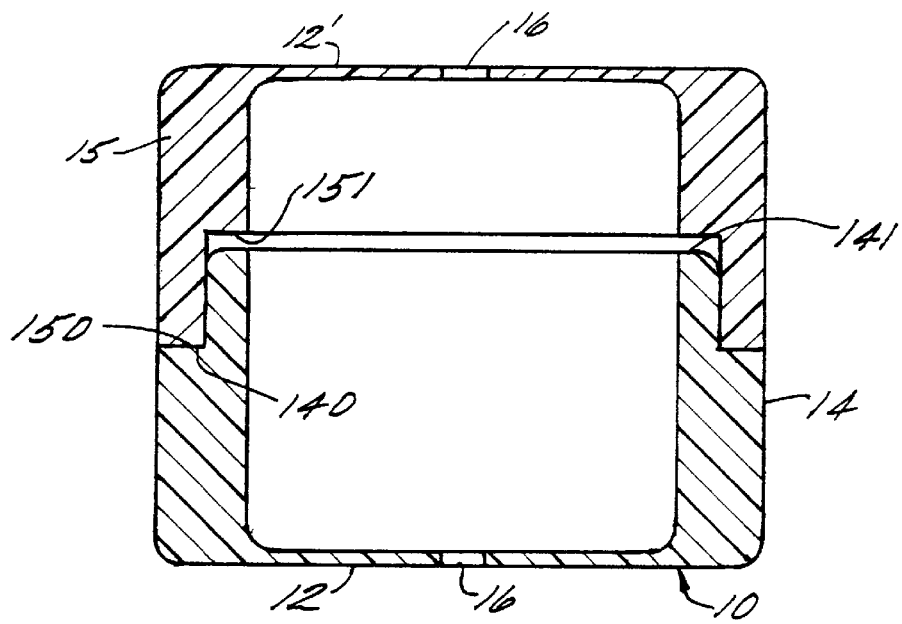
FIG. 2 represents a longitudinal cut view of the same acoustic valve.

In one refers to FIGS. 1 and 2, one can see that in a first method of production, the acoustic valve of the invention presents a cylindrical form and comprises two tubular pieces 10 and 11 roughly of the same dimensions.

Each piece 10, 11 is produced by molding a plastic material or epoxy resin and contains a disk 12, 12' forming one end of a hollow cylinder 14, 15 open at its other end and of which the perimeter edge 140, 150 contains a shouldering wall 141, 151. The two shouldering walls 141, 151 are complementary and opposite from each other in order to allow the assembly of the two pieces 10, 11 by interlocking and gluing.

The rigid planar disks forming the ends of the cylinder are spaced axially opposite each other and are positionally fixed. Each disk 12, 12' has a diameter between 2 and 4mm, and contains at its center a circular orifice 16 of which the diameter is between 0.2 and 0.6 mm.

The dimensions of the pieces 10 and 11 are determined in a manner such that the distance separating the two disks 12 and 12' after assembly of the pieces 10, 11 is between 2 and 7 mm.

The disks 12 and 12' can also contain a plurality of borings, of which the diameter would be determined in such a manner that the total surface of the borings is roughly equal to that of the central boring 16.

Figure 3A:
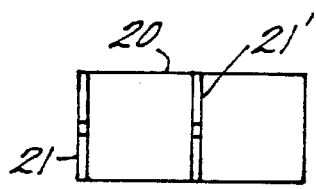
FIG. 3a represents a longitudinal schematic view of a second embodiment of the valve according to the invention.

If one refers now to FIG. 3*a*, one can see that in a second embodiment of the invention, the valve is made up of a tube 20 enclosing two disks 21 and 21', pierced at their centers and roughly of the same diameter as the internal diameter of the tube 20, of which one disk 21 is positioned. at one of the ends of the tube 20 and the other disk 21' is set back from the opposite end.

Figure 3B:
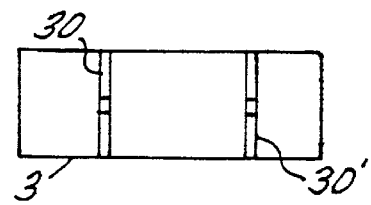
FIG. 3b represents a longitudinal schematic view of a third embodiment of the valve according to the invention.

If one refers to FIG. 3*b*, one can see that, in a third embodiment, the acoustic valve comprises a tube 3 enclosing two disks 30 and 30' pierced at their centers and each set back from one end of the tube 3.

In each of these two latter embodiments, the dimensions of the disks and the distance that separates the disks axially is within the same limits as those of the first embodiment.

The acoustic valve of the invention is designed to be inserted into a perforated ear plug preferably made of an elastic material in view of its placement in the external auditory canal of a user.

The dimensions, defined above, of the acoustic valve of the invention allow an efficient non-linear sound reduction to be obtained, the reduction of the sound increasing with the level of the exterior noise instantaneously, especially above the sound level of 110 db SPL.

The acoustic valve of the invention allows users to communicate between themselves while locating and identifying sources of sound representative of human speech and low level noises in the environment, and reducing sudden noises, for example, the noise from fire arms of all calibers or from industrial machines, such as metallurgical presses.

What is claimed is:

1. An acoustic valve capable of selective and non-linear filtering of sound and placeable in a perforated ear plug, said valve comprising a cylindrical tube enclosing two rigid planar disks spaced axially opposite each other and fixedly positioned within said cylindrical tube, wherein said disks contain at least one perforation each.

2. The acoustic valve according to claim 1 further comprising two hollow, cylindrical parts, wherein each cylindrical part is closed at one end by one of said rigid disks containing said perforation and open at the other end, the peripheral edge of each open end of each cylindrical part being configured to be fixedly attached to the open end of the other cylindrical part.

3. The acoustic valve according to claim 2 wherein said valve comprises a plastic material.

4. An acoustic valve capable of selective and non-linear filtering of sound and placeable in a perforated ear plug, said valve comprising a cylindrical tube enclosing two rigid disks spaced axially opposite each other, said cylindrical tube comprising two hollow, cylindrical parts, each of said parts being closed at one end by one of said disks and being open at the other end, the peripheral edge of each open end of each cylindrical part being configured to be fixedly attached to the open end of the other cylindrical part, and wherein said disks contain at least one perforation each, the thickness of said disks being between 0.05 and 0.5 mm.

5. An acoustic valve capable of selective and non-linear filtering of sound and placeable in a perforated ear plug, said valve comprising a cylindrical tube enclosing two rigid disks spaced axially opposite each other, wherein said disks contain at least one perforation each, and wherein the total perforated surface area of at least one disk is between 0.05 and 0.5 $mm^2$.

6. The acoustic valve according to claim 1 wherein said valve comprises a plastic material.

7. An acoustic valve capable of selective and non-linear filtering of sound and placeable in a perforated ear plug, said valve comprising a cylindrical tube enclosing two rigid disks spaced axially opposite each other, wherein said disks contain at least one perforation each, and wherein the thickness of said disks is between 0.05 and 0.5 mm.

* * * * *